(12) United States Patent
Bessho

(10) Patent No.: US 7,561,660 B2
(45) Date of Patent: Jul. 14, 2009

(54) RADIATION CT SYSTEM AND DATA ACQUISITION SYSTEM

(75) Inventor: Koji Bessho, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 228 days.

(21) Appl. No.: 11/402,495

(22) Filed: Apr. 12, 2006

(65) Prior Publication Data
US 2007/0025502 A1 Feb. 1, 2007

(30) Foreign Application Priority Data
Apr. 14, 2005 (JP) .............................. 2005-116637

(51) Int. Cl.
*G01N 23/00* (2006.01)
(52) U.S. Cl. ............................................. 378/19; 378/4
(58) Field of Classification Search .................... 378/4, 378/15, 16, 19, 98.8, 146, 901
See application file for complete search history.

(56) References Cited

U.S. PATENT DOCUMENTS

| | | | |
|---|---|---|---|
| 5,218,533 A | 6/1993 | Schanen | |
| 5,220,589 A | 6/1993 | Gard | |
| 6,081,576 A | 6/2000 | Schanen et al. | |
| 6,324,244 B1 * | 11/2001 | Lauter et al. | 378/4 |
| 6,362,478 B1 | 3/2002 | McDaniel et al. | |
| 6,760,404 B2 * | 7/2004 | Saito et al. | 378/98.8 |
| 7,139,367 B1 * | 11/2006 | Le | 378/98 |
| 7,191,093 B2 * | 3/2007 | Hein et al. | 702/182 |
| 7,215,801 B2 * | 5/2007 | Bueno et al. | 382/128 |
| 7,295,689 B2 * | 11/2007 | Dixon | 382/128 |
| 2001/0005409 A1 * | 6/2001 | Gohno et al. | 378/19 |
| 2001/0028697 A1 * | 10/2001 | Nahaliel et al. | 378/19 |
| 2002/0071518 A1 * | 6/2002 | Bruder et al. | 378/19 |
| 2002/0181648 A1 * | 12/2002 | Ruetten et al. | 378/19 |

FOREIGN PATENT DOCUMENTS

| | | |
|---|---|---|
| EP | 1260811 A2 | 11/2002 |
| JP | 05072556 | 10/1986 |
| JP | 2001-212128 | 8/2001 |

* cited by examiner

*Primary Examiner*—Irakli Kiknadze
(74) *Attorney, Agent, or Firm*—Armstrong Teasdale LLP

(57) ABSTRACT

A CT system including a multi-array detector that includes a plurality of detector cell, a data acquisition system that acquires data items representing doses of radiation incident on the detector according to output signals of the detector cells, and a data processing unit that identifies a distribution of doses of radiation incident on the detector, which is used to construct tomographic images acquired by the data acquisition system. The data acquisition system includes a smaller number of amplifiers, which amplify signals produced by the detector cells and transmit the resultant signals, than the number of detector elements, and a switching unit that changes the continuities between the detector cells and amplifiers so that detector cells whose signals are amplified by each of the amplifiers will be changed into others juxtaposed in the direction of slices during the scanning of a subject.

20 Claims, 9 Drawing Sheets

First View Angle <tab> Second View Angle <tab> i-th View Angle

MODE A

MODE B

RADIATION CT SYSTEM AND DATA ACQUISITION SYSTEM

CROSS REFERENCE TO RELATED APPLICATIONS

This application claims the benefit of Japanese Application No. 2005-116637 filed Apr. 14, 2005.

BACKGROUND OF THE INVENTION

The present invention relates to a radiation CT system such as an X-ray CT system, a data acquisition system, and a data acquisition method.

Radiation CT systems employing a multi-array detector that has a plurality of detector elements set in array in a direction of channels and in a direction of slices alike are known (refer to, for example, Patent Document 1). Output signals of the detector elements are amplified by amplifiers included in a data acquisition system (DAS). In general, the number of amplifiers is the same as the number of detector elements (the number of channels by the number of arrays juxtaposed in the direction of slices).

Patent Document 1 describes that four data acquisition systems (DASs) are used in combination with a multi-array detector having eight arrays of detector elements juxtaposed in the direction of slices, that the connections between the arrays of detector elements and the data acquisition systems are changed based on a slice thickness, and that one amplifier amplifies outputs of two arrays of detector elements. Herein, the connections are changed from ones to others prior to scanning, and two arrays of detector elements are treated as one array of detector elements. This is equivalent to a case where the same number of amplifiers as the number of detector elements is included.

[Patent Document 1] Japanese Unexamined Patent Publication No. 2001-212128

As for a multi-array detector, an increase in the number of arrays of detector elements juxtaposed in the direction of slices or realization of finer detector elements, that is, an increase in the number of detector elements is demanded from the viewpoint of a shorter scan time or improved image quality. On the other hand, amplifiers are included in a data acquisition system in association with all detector elements. The number of amplifiers increases along with an increase in the number of detector elements, whereby various drawbacks take place. For example, it is hard to preserve a space in which the amplifiers are disposed, a power consumption increases, an amount of dissipated heat increases, and a cost increases.

SUMMARY OF THE INVENTION

An object of the present invention is to provide a radiation CT system, a data acquisition system, and a data acquisition method which make it possible to decrease the number of amplifiers.

According to the first aspect of the present invention, there is provided a radiation CT system that scans a subject by rotating a radiation source, which irradiates radiation to the subject, about the subject's body axis, and that constructs tomographic images of the subject on the basis of a distribution of doses of the radiation which are used to produce a plurality of views. The radiation CT system includes: a multi-array detector that has a plurality of detector elements, each of which converts the radiation into an electric signal and transmits the electric signal, set in array in a direction of channels that is a direction around the body axis and in a direction of slices that is a direction parallel to the body axis, and that is opposed to the radiation source with the subject between them; a data acquisition system that acquires data items representing the doses of the radiation incident on the multi-array detector on the basis of output signals of the plurality of detector elements; and a data processing unit that identifies a distribution of the doses of the radiation incident on the multi-array detector, which is used to construct the tomographic images, according to the data items acquired by the data acquisition system. The data acquisition system includes a plurality of amplifiers that numbers a smaller value than the plurality of detector elements does and that amplifies signals produced by the plurality of detector elements and transmits the resultant signals, and a switching means that changes the continuities between the plurality of detector elements and the plurality of amplifiers so that detector elements whose signals are amplified by each of the plurality of amplifiers will be changed into others, which are juxtaposed in the direction of slices, during scanning of the subject.

Preferably, the switching means changes the continuities between the plurality of detector elements and the plurality of amplifiers for each production of a view.

Preferably, the switching means changes the continuities between the plurality of detector elements and the plurality of amplifiers so as to cyclically alternate a plurality of modes in which different continuities are established.

Preferably, the switching means assigns the plurality of amplifiers to amplifications of signals produced by the plurality of detector elements so that each of the plurality of amplifiers will amplify a signal made by synthesizing signals produced by a predetermined number of detector elements successively juxtaposed in the direction of slices. The switching means changes the continuities between the plurality of detector elements and the plurality of amplifiers so that every time the modes are switched, the predetermined number of detector elements assigned to each of the amplifiers will be changed into a predetermined number of detector elements that is partly identical to the predetermined number of detector elements and that is juxtaposed in the direction of slices. The data processing unit calculates a dose of radiation incident on a smaller number of detector elements than the predetermined number of detector elements according to the data items representing doses of radiation incident on predetermined numbers of detector elements which are acquired by the data acquisition unit.

Preferably, the switching means changes the continuities between the plurality of detector elements and the plurality of amplifiers so that every time the modes are switched, the predetermined number of detector elements assigned to each of the amplifiers will be changed into a predetermined number of detector elements that is different from the predetermined number of detector elements in one detector element thereof and that is juxtaposed in the direction of slices. The data processing unit calculates a dose of radiation incident on each detector element according to the data items representing doses of radiation incident on predetermined numbers of detector elements which are acquired by the data acquisition unit.

Preferably, the data processing unit accumulates doses of radiation incident on predetermined numbers of detector elements which include a specific detector element and which are grouped in the plurality of modes that is cyclically alternated. The data processing unit subtracts a correction value which is calculated based on doses of radiation incident on predetermined numbers of detector elements which do not include the specific detector element but are partly identical to the predetermined numbers of detector elements including the specific detector, from the result of the accumulation, and thus works out a dose of radiation incident on the specific detector element.

Preferably, the predetermined number of detector elements refers to two detector elements and the number of modes is two. The switching means changes the continuities between the plurality of detector elements and the plurality of amplifiers so that a synthetic signal composed of a signal produced by a first detector element and a signal produced by a second detector element, and a synthetic signal composed of a signal produced by a third detector element and a signal produced by a fourth detector element will be amplified in the first mode, and that a synthetic signal composed of a signal produced by the second detector element and a signal produced by the third detector element, and a signal produced by the fourth detector element and a signal produced by a fifth detector element will be amplified in the second mode. Assuming that $A_{12}$ denotes a dose of radiation incident on the first and second detector elements in the first mode, $A_{34}$ denotes a dose of radiation incident on the third and fourth detector elements in the first mode, $B_{23}$ denotes a dose of radiation incident on the second and third detector elements in the second mode, and $B_{45}$ denotes a dose of radiation incident on the fourth and fifth detector elements in the second mode, the data processing unit calculates a dose $A_3$ of radiation incident on the third detector element in the first mode according to the following expression:

$$A_3 = (A_{34} + B_{23})/2 - (A_{12} + B_{45})/4$$

Preferably, the switching means changes the continuities between the plurality of detector elements and the plurality of amplifiers so that a synthetic signal composed of a signal produced by a detector element, which is located at an end of a channel extending in the direction of slices, and a signal produced by a detector element, which is located at an end of an adjoining channel will be amplified in one mode, and a synthetic signal composed of a signal produced by the detector element located at the end of the channel, and a signal produced by a detector element belonging to the channel will be amplified in the other mode.

Preferably, the data acquisition system acquires data at a frequency that corresponds to a product of the frequency, at which an ordinary X-ray CT system that does not change the continuities between a plurality of amplifiers and a plurality of detector elements should produce a view so as to ensure predetermined image quality, by the number of modes, and thus provides image quality equivalent to the predetermined image quality.

Preferably, the amplifiers each include an integrating circuit that integrates a signal produced by a detector element. The switching means performs mode switching concurrently with resetting of the integrating circuits.

Preferably, the switching means includes field-effect transistors.

Preferably, the switching means includes a plurality of switching circuits interposed between the plurality of detector elements and the plurality of amplifiers. Each of the switching circuits includes: a first n-channel field-effect transistor having a source thereof connected to a detector element and having a drain thereof connected to an amplifier; a second p-channel field-effect transistor having a source thereof connected to the detector element, having a drain thereof connected to the amplifier, and having a gate thereof connected to the gate of the first field-effect transistor; and an inverter that inverts a signal to be applied to either of the gates of the first and second field-effect transistors.

According to the second aspect of the present invention, there is provided a radiation CT system that scans a subject by rotating about the subject's body axis a radiation source which irradiates radiation to the subject, and constructs tomographic images of the subject according to a distribution of doses of the radiation which are used to produce a plurality of views. The radiation CT system includes: a multi-array detector that has a plurality of detector elements, each of which converts the radiation into an electric signal and transmits the electric signal, set in array in a direction of channels that is a direction around the body axis and in a direction of slices that is a direction parallel to the body axis, and that is opposed to the radiation source with the subject between them; a data acquisition system that acquires data items representing doses of radiation incident on the multi-array detector according to output signals of the plurality of detector elements; and a data processing unit that identifies a distribution of doses of radiation incident on the multi-array detector, which is used to construct the tomographic images, according to the data items acquired by the data acquisition unit. The data acquisition system includes: a plurality of amplifiers that numbers a smaller value than the plurality of detector elements does and that amplifies signals produced by the plurality of detector elements and transmits the resultant signals; and a switching means that assigns the plurality of amplifiers to amplifications of signals produced by the plurality of detector elements so that each of the plurality of amplifiers will amplify a signal made by synthesizing signals produced by a predetermined number of detector elements successively juxtaposed in the direction of slices, and that changes the continuities between the plurality of detector elements and the plurality of amplifiers so that the predetermined number of detector elements assigned to each of the amplifiers will be changed into a predetermined number of detector elements that is partly identical to the predetermined number of detector elements and that is juxtaposed in the direction of slices.

According to the third aspect of the present invention, there is provided a data acquisition system that is included in a radiation CT system in which: a radiation source that irradiates radiation to a subject and a multi-array detector that has a plurality of detector elements, each of which converts the radiation into an electric signal and transmits the electric signal, set in array in a direction of channels that is a direction around the subject's body axis and in a direction of slices that is a direction parallel to the body axis, and that is opposed to the radiation source with the subject between them are rotated about the subject's body axis in order to scan the subject; and tomographic images of the subject are constructed based on a distribution of doses of radiation which are used to produce a plurality of views. The data acquisition system acquires data items representing doses of radiation incident on the multi-array detector which are used to construct the tomographic images. The data acquisition system includes: a plurality of amplifiers that numbers a smaller value than the plurality of detector elements does and that amplifies signals produced by the plurality of detector elements and transmits the resultant signals; and a switching means that changes the continuities between the plurality of detector elements and the plurality of amplifiers so that detector elements whose signals are amplified by each of the plurality of amplifiers will be changed into others juxtaposed in the direction of slices during scanning of the subject.

According to the fourth aspect of the present invention, there is provided a data acquisition system included in a radiation CT system in which: a radiation source that irradiates radiation to a subject and a multi-array detector that has a plurality of detector elements, each of which converts the radiation into an electric signal and transmits the electric signal, set in array in a direction of channels that is a direction around the subject's body axis and in a direction of slices that is a direction parallel to the body axis, and that is opposed to the radiation source with the subject between them are rotated about the subject's body axis in order to scan the subject; and tomographic images of the subject are constructed based on a distribution of doses of radiation which are used to produce a plurality of views. The data acquisition system acquires data items representing doses of radiation incident on the multi-array detector which are used to construct the tomographic images. The data acquisition system includes: a plurality of amplifiers that numbers a smaller value than the plurality of detector elements does and that amplifies signals produced by the plurality of detector elements and transmits the resultant signals; and a switching means that assigns the plurality of amplifiers to amplifications of signals produced by the plurality of detector elements so that each of the plurality of amplifiers will amplify a signal made by synthesizing signals produced by a predetermined number of detector elements successively juxtaposed in the direction of slices, and that changes the continuities between the plurality of detector elements and the plurality of amplifiers so that the predetermined number of detector elements assigned to each of the amplifier will be changed to a predetermined number of detector elements which is partly identical to the predetermined number of detector elements and which is juxtaposed in the direction of slices.

According to the fifth aspect of the present invention, there is provided a data acquisition method in which: a radiation source that irradiates radiation to a subject and a multi-array detector that has a plurality of detector elements, each of which converts the radiation into an electric signal and transmits the electric signal, set in array in a direction of channels that is a direction around the subject's body axis and in a direction of slices that is a direction parallel to the body axis, and that is opposed to the radiation source with the subject between them are rotated about the subject's body axis in order to scan the subject; and data items representing doses of radiation incident on the multi-array detector are acquired based on output signals of the plurality of detector elements. A plurality of amplifiers that numbers a smaller value than the plurality of detector elements does and that amplifies signals produced by the plurality of detector elements and transmits the resultant signals is included. The continuities between the plurality of detector elements and the plurality of amplifiers are changed so that detector elements whose signals are amplified by each of the plurality of amplifiers will be changed into others juxtaposed in the direction of slices during scanning of the subject.

According to the present invention, the number of amplifiers can be decreased.

Further objects and advantages of the present invention will be apparent from the following description of the preferred embodiments of the invention as illustrated in the accompanying drawings.

DETAILED DESCRIPTION OF THE INVENTION

Figure 1:
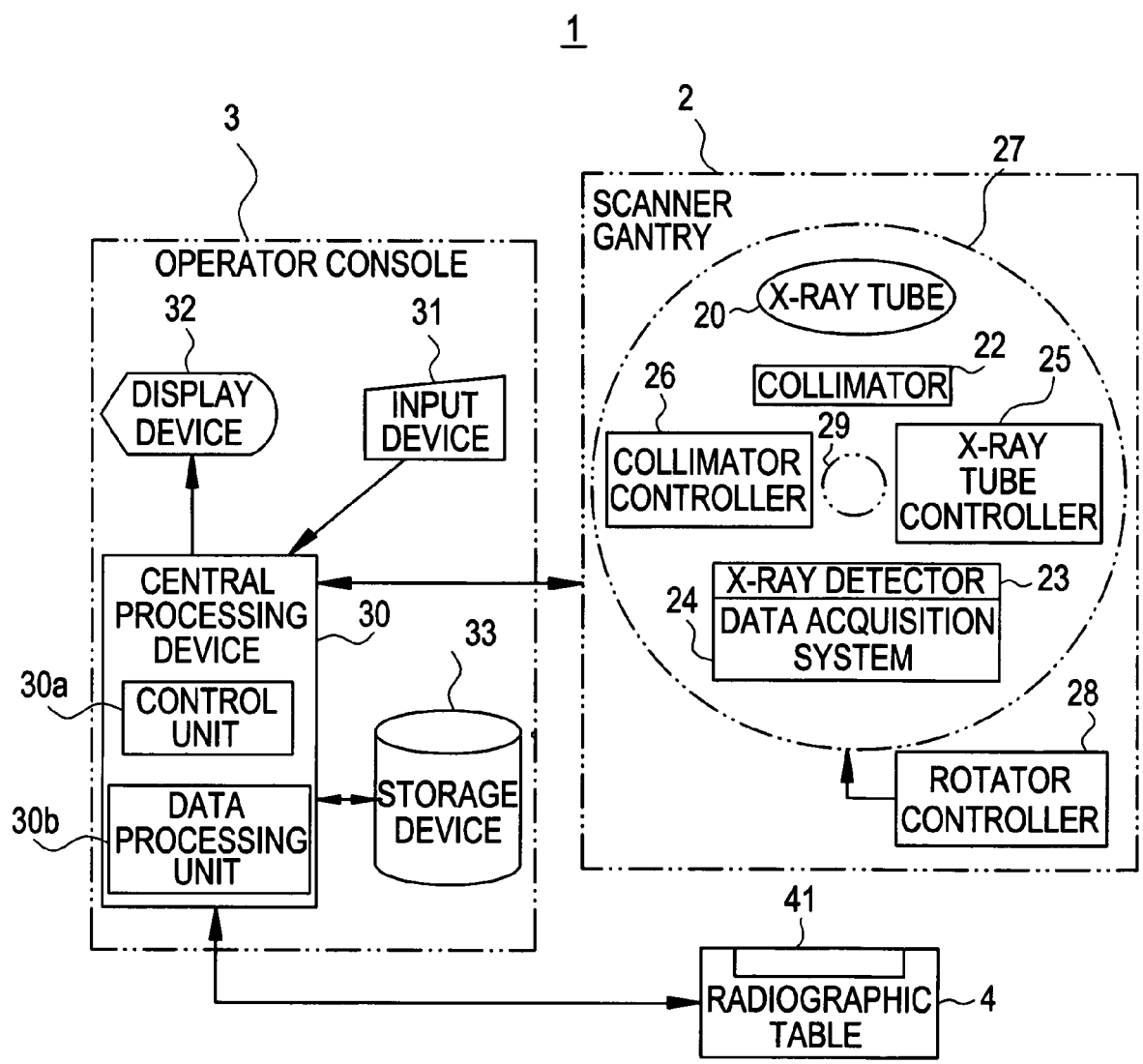
FIG. 1 is a block diagram showing the configuration of an X-ray CT system in accordance with an embodiment of the present invention.
Figure 2A:
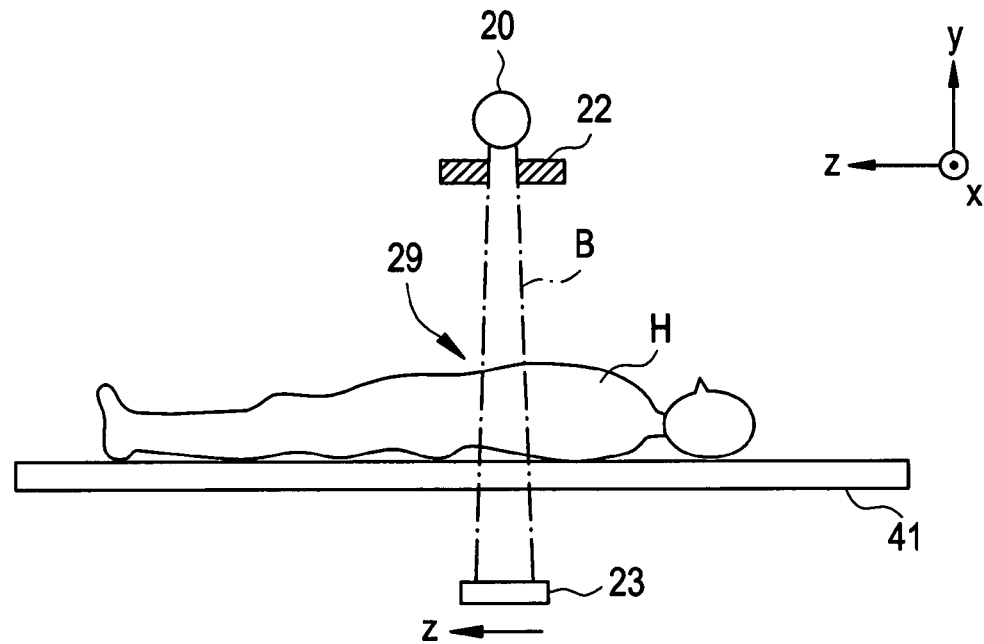
FIGS. 2a and 2b schematically show a state of radiography performed by the X-ray CT system shown in FIG. 1.
Figure 2B:
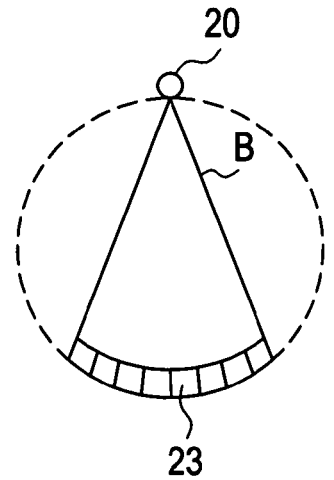
Figure 2B:
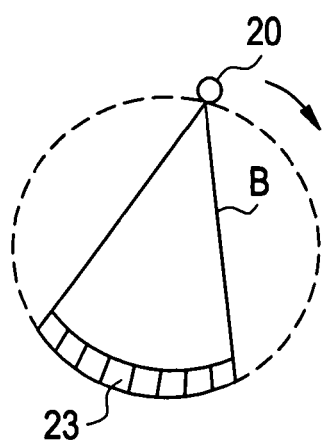
Figure 2B:
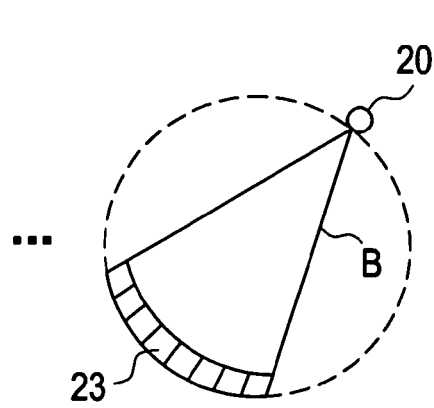

FIG. 1 is a block diagram showing the overall configuration of an X-ray CT system 1 that is a radiation CT system in accordance with an embodiment of the present invention. FIG. 2(a) and FIG. 2(b) schematically show a state of radiography performed by the X-ray CT system 1.

The X-ray CT system 1 is designed as a CT system that acquires projection data items produced by performing so-called helical scanning on a subject at a plurality of view angles, and reconstructs images according to the projection data items. The present invention can be applied to an X-ray CT system that adopts any scanning technique other than the helical scanning.

The X-ray CT system 1 includes a scanner gantry 2, an operator console 3, and a radiographic table 4.

The scanner gantry 2 includes an X-ray tube 20 serving as a radiation source, a collimator 22 that reshapes radiation radiated from the X-ray tube 20, an X-ray detector 23 that detects X-rays radiated from the X-ray tube 20 and produces an electric signal proportional to a detected X-ray dose, a data acquisition system (DAS) 24 that acquires projection data items produced based on the electric signals sent from the X-ray detector 23, an X-ray tube controller 25 that drives or controls the X-ray tube 20, and a collimator controller 26 that drives or controls the collimator 22.

The scanner gantry 2 further includes a rotator 27 that accommodates the X-ray tube 20 and X-ray detector 23 and rotates together with them, and a rotator controller 28 that drives or controls the rotator 27. The scanner gantry 2 has a bore 29 into which a subject is carried, and has the X-ray tube 20 and X-ray detector 23 opposed to each other with the bore 29 between them.

The operator console 3 includes an input device 31 that transmits a signal responsively to an operator's manipulation, a central processing device 30 that performs various pieces of processing, which include image reconstruction based on projection data items acquired by the data acquisition system 24, according to signals sent from various apparatuses including the input device 31 and scanner gantry 2, a display device 32 on which CT images reconstructed by the central processing device 30 are displayed, and a storage device 33 in which programs according to which the central processing device 30 performs processing, data items, and X-ray CT images are stored.

The radiographic table 4 includes a cradle 41 that is moved into or out of the bore 29 of the scanner gantry 2 with a subject lying down thereon. The cradle 41 is driven by a servomotor that is not shown and that is incorporated in, for example, the radiographic table 4. The servomotor is controlled based on a control signal sent from the central processing device 30 via a servo amplifier that is not shown.

The central processing device 30 includes a control unit 30*a* that drives or controls the X-ray tube 20, collimator 22, rotator 27, and cradle 41 via the X-ray tube controller 25, collimator controller 26, rotator controller 28, and servo amplifier incorporated in the radiographic table 4 respectively, and a data processing unit 30*b* that processes data acquired by the data acquisition system 24. The control unit 30*a* and data processing unit 30*b* are implemented when the central processing device 30 runs any of programs stored in the storage device 33 or the like. The central processing device 30 further includes processing units that implement various functions including image reconstruction based on data items processed by the data processing unit 30*b*. The processing units may be appropriately realized according to known technologies.

As shown in FIG. 2(*b*), the X-ray tube 20 and X-ray detector 23 rotate about the body axis (z axis) of a subject H. As shown in FIG. 2(*a*), the cradle 41 carries the subject in the direction of the body axis. Consequently, the X-ray tube 20 and X-ray detector are helically moved relatively to the subject H.

While the X-ray tube 20 and X-ray detector are rotated about the subject's body axis, the data acquisition system 24 acquires data items at each view angle. As shown in FIG. 2(*b*), each view angle is set to a certain angle of rotation. In general, one thousand view angles are designated for one turn of the scanner gantry in order to produce one thousand views. In the X-ray CT system 1, two thousand view angles are designated as described later.

Figure 3:
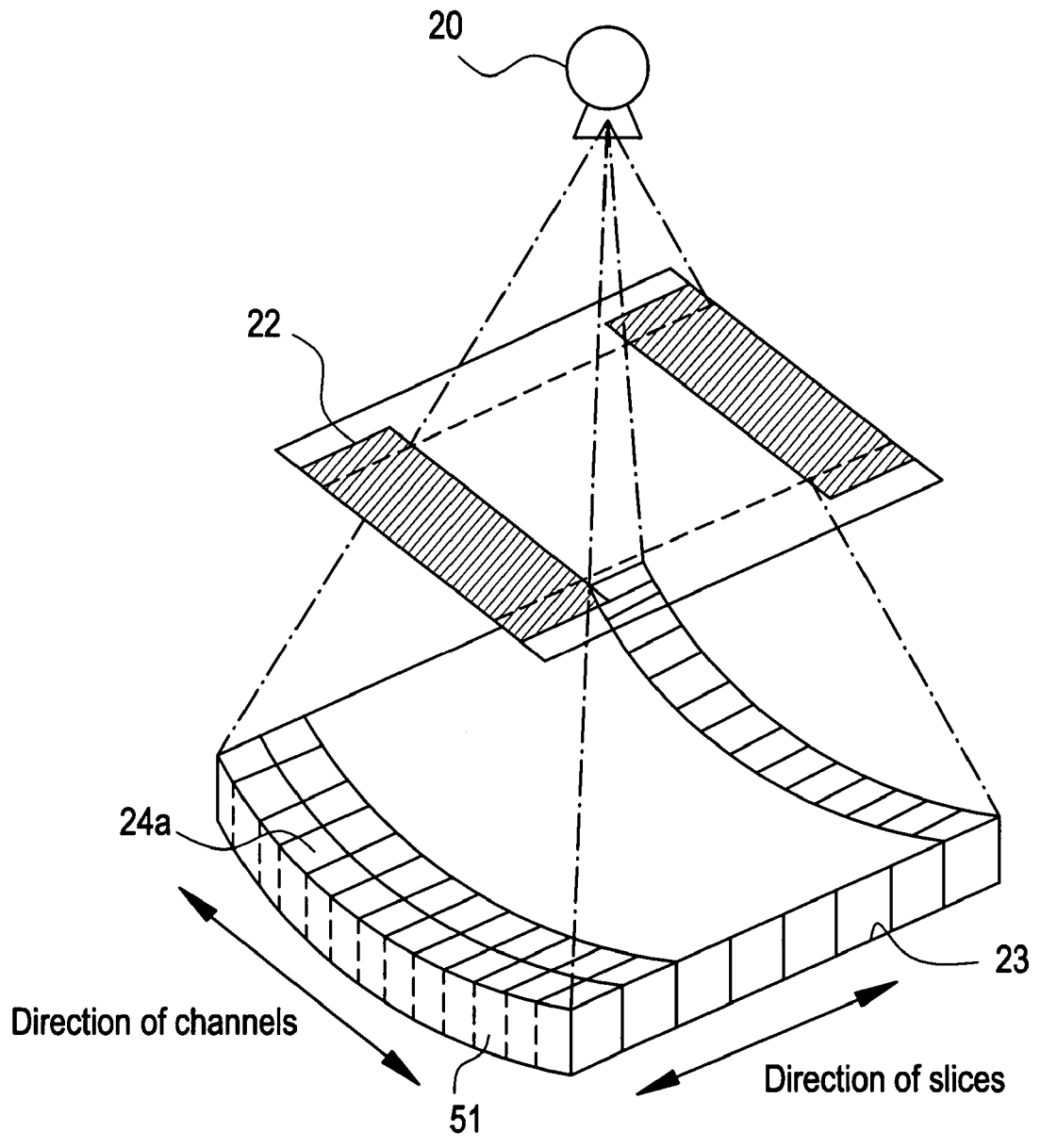
FIG. 3 is a perspective view schematically showing an arrangement involved in X-ray detection and included in the X-ray CT system shown in FIG. 1.

FIG. 3 is a perspective view schematically showing an arrangement involved in X-ray detection and included in the X-ray CT system 1. The X-ray tube 20 irradiates X-rays of a predetermined intensity to a scan field in a subject according to a control signal sent from the X-ray controller 25. The collimator 22 is interposed between the X-ray tube 20 and the detector 23, and reshapes X-rays radiated from the X-ray tube 20 according to a control signal sent from the collimator controller 26. The X-rays reshaped by the collimator 22 pass through the subject and reach the detector 23.

The detector 23 is realized with a so-called multi-array detector and has a plurality of detector cells (detector elements) 51 set in array in a direction of channels (a direction around the body axis or an x-axis direction in FIG. 3) and in a direction of slices (a body-axis direction or a z direction). For example, one thousand detector cells 51 are juxtaposed in the direction of channels, and four to sixty-four detector cells 51 are juxtaposed in the direction of slices. The detector 23 has a detection surface 24*a* thereof, on which X-rays fall, curved like an arc in the direction of channels.

Figure 4A:
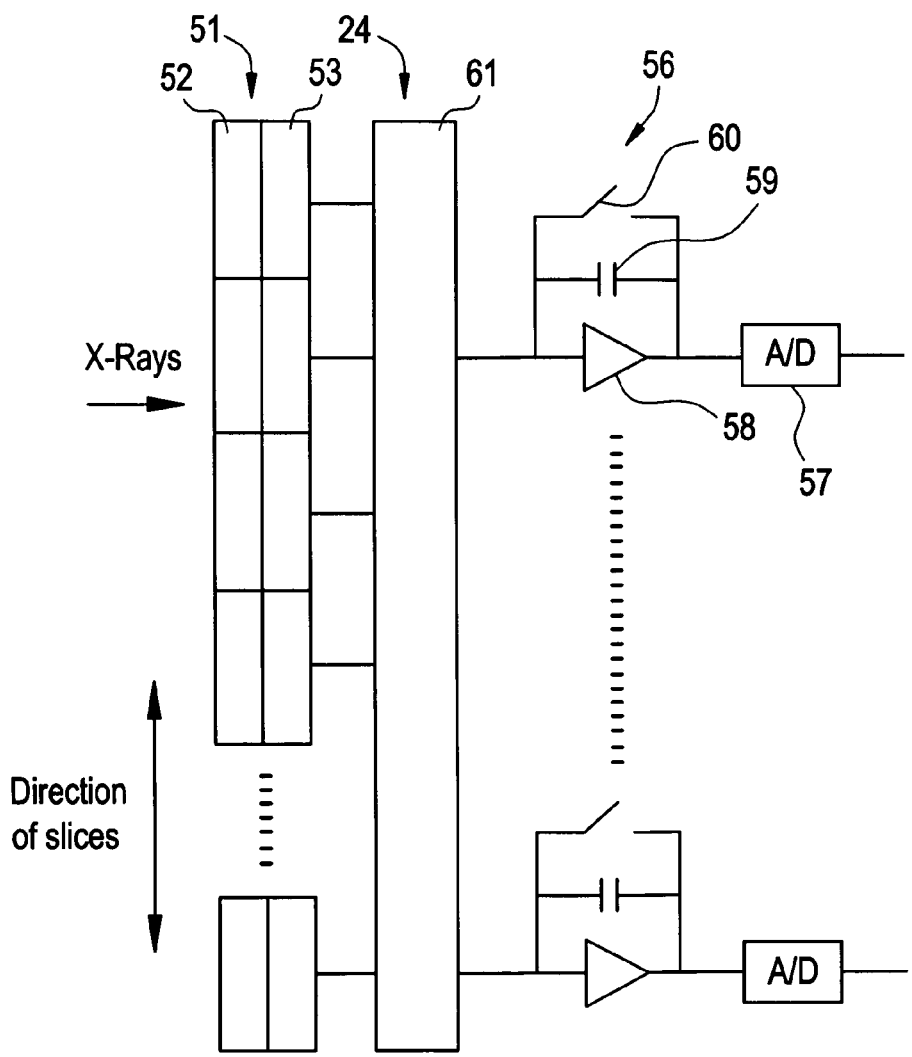
FIGS. 4a and 4b include circuit diagrams detailing a data acquisition system included in the X-ray CT system shown in FIG. 1.
Figure 4B:
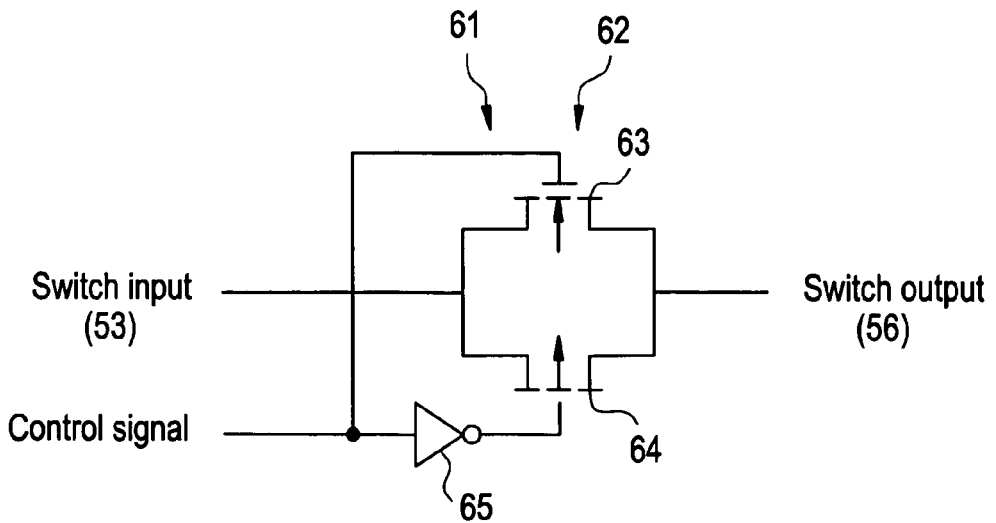

FIG. 4(*a*) is a circuit diagram detailing the detector cells 51 and data acquisition system 24. In FIG. 4(*a*), part of the data acquisition system 24 through which signals produced by detector cells juxtaposed in the direction of slices are propagated is shown, but part thereof through which signals produced by detector cells juxtaposed in the direction of channels are propagated is not shown.

The detector cells 51 each include a scintillator 52 and a photoelectric transducer 53 such as a photodiode. X-rays radiated from the X-ray tube 20 are incident on the scintillator 52 and converted into light. The resultant light is received by the photodiode 53, and an electric signal proportional to an amount of received light is transferred to the data acquisition system 24.

The data acquisition system 24 includes amplifiers 56 each of which amplifies an electric signal sent from the detector cell 51, and A/D converters 57 each of which analog-to-digital converts the electric signal amplified by the amplifier 56. Furthermore, the data acquisition system 24 includes a switching unit 61 that changes the continuities between the detector cells 51 and amplifiers 56.

The number of amplifiers 56 assigned to each channel is smaller than the number of arrays of detector cells 51 juxtaposed in the direction of slices. Specifically, the number of amplifiers 56 assigned to each channel is a half of the number of arrays of detector cells juxtaposed in the direction of slices. Namely, the sum total of amplifiers 56 is a product of the number of channels by the half of the number of arrays of detector cells juxtaposed in the direction of slices.

The amplifiers 56 each include, for example, an operational amplifier 58, a capacitor 59 connected in parallel with the operational amplifier 58, and a switch 60 connected in parallel with the capacitor 59. Consequently, the amplifiers 56 serve as integrating circuits. An output signal of the detector cell 51 is integrated during a time equivalent to the time constant of the capacitor 59 having a certain capacitance. When the switch 60 is turned on, the charge stored in the capacitor 59 is released and the amplifier is reset.

The number of A/D converters 57 juxtaposed in the direction of slices is the same as the number of amplifiers 56 juxtaposed in the direction of slices. Alternatively, the number of A/D converters 57 may be smaller than the number of amplifiers 56, and multiplexers may be interposed between the amplifiers 56 and the A/D converters 57. The same applies to A/D converters juxtaposed in the direction of channels.

The switching unit 61 is interposed between the detector cells 51 and the amplifiers 56, and changes the continuities between the detector cells 51 and the amplifiers 56. The switching unit 61 includes, for example, field-effect transistors (FETs). When a bias input device that is not shown applies a predetermined voltage according to a control signal sent from the control unit 30*a* included in the central processing device 30, the switching unit 61 enables or disables the detector cells 51 and amplifiers 58 to conduct or from conducting.

FIG. 4(*b*) is a circuit diagram detailing part of the switching unit 61. The switching unit 61 includes a plurality of switching circuits 62. The switching circuits 62 each include an n-channel MOSFET 63, a p-channel MOSFET 64, and an inverter 65 that inverts a control signal to be applied to the FET 64. The source of the FET 63 and the source of the FET 64 are connected to one photodiode 53, and the drain of the FET 63 and the drain of the FET 64 are connected to one amplifier 56.

When a high-level control signal is transferred to the FET 63, it is applied to the gate of the FET 63 as it is. The control signal is inverted and then applied to the gate of the FET 64. This causes the FET 63 and FET 64 to conduct. In contrast, when a low-level control signal is transferred to the FET 63, the FET 63 and FET 64 become non-conducting.

FIG. 5 includes conceptual diagrams showing a mode switching method implemented in the switching unit 61. FIG. 5 shows two channels each of which includes sixteen detector cells 51. The vertical direction in the sheet of paper of the drawing corresponds to the direction of slices, and the lateral direction therein corresponds to the direction of channels. As for the amplifiers 56, only amplifiers connected to the detector cells 51 belonging to the right-hand channel in the sheet of paper of the drawing are shown, but those connected to the detector cells 51 belonging to the left-hand channel therein are not shown.

Figure 5A:
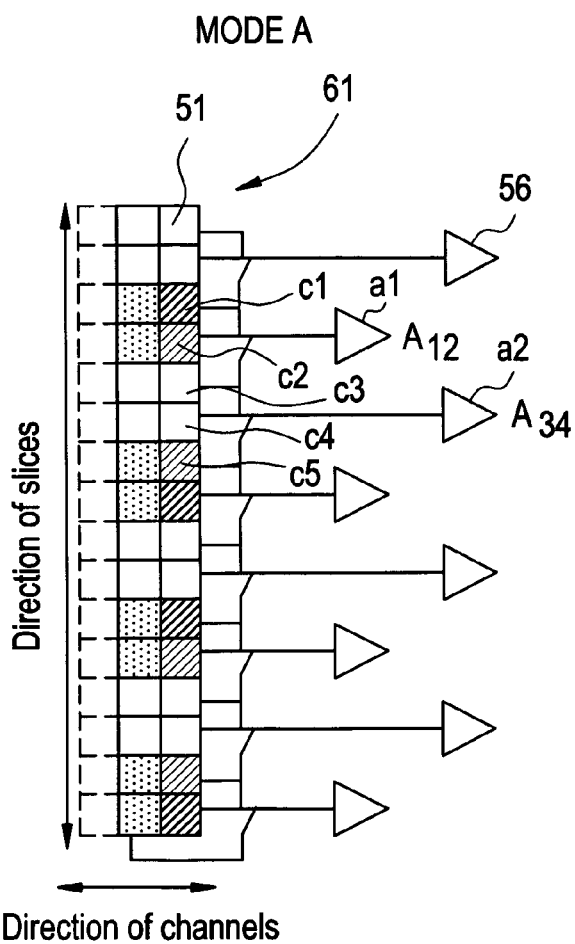
FIGS. 5a and 5b include conceptual diagrams showing a mode switching method implemented in the X-ray CT system shown in FIG. 1.
Figure 5B:
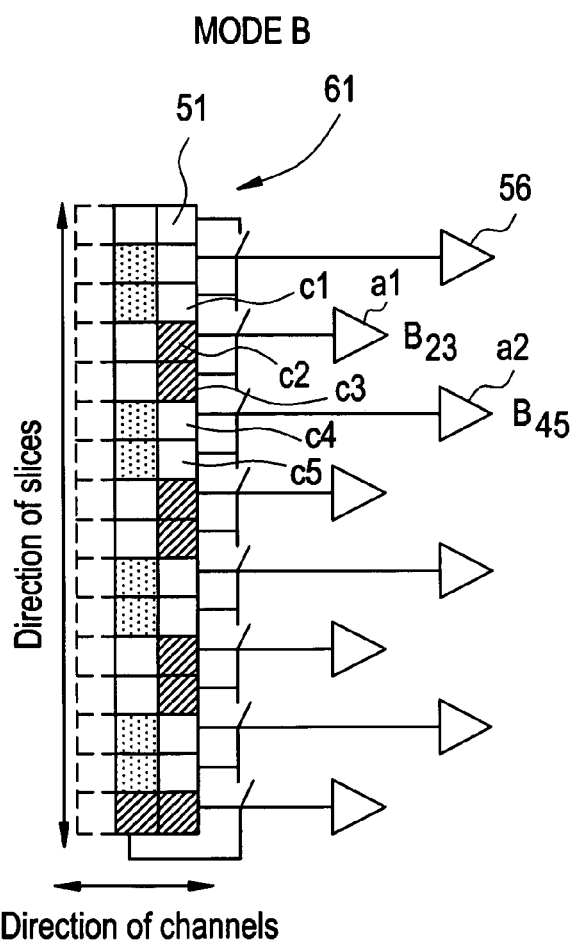

The switching unit 61 switches the continuities between the detector cells 51 and amplifiers 56 according to whichever of mode A shown in FIG. 5(a) and mode B shown in FIG. 5(b) is selected. In either of the modes, signals produced by two detector cells 51 are synthesized and transferred to one amplifier 56. The modes A and B in which different continuities are established are switched so that a value detected by each detector cell 51 is calculated based on a difference between a value detected in mode A and a value detected in mode B. A concrete procedure will be described below.

As shown in FIG. 5(a), in mode A, the detector cells 51 belonging to a channel that extends in the direction of slices are sequentially paired from the end of each channel (an end in the vertical direction in the sheet of paper). Each pair of detector cells 51 is connected to one amplifier 56. On the other hand, in FIG. 5(b), one of detector cells 51 to be paired is different from one of those in mode A. Incidentally, a detector cell 51 at an end of each channel is paired with a detector cell 51 at an end of an adjoining channel, and the pair of detector cells is connected to one amplifier 56.

Assume that reference numerals c1 to c5 denote the detector cells 51 and reference numerals a1 and a2 denote the amplifiers 56. In mode A, the amplifier a1 amplifies a signal $A_{12}$ made by synthesizing signals produced by the detector cells c1 and c2, and transmits the resultant signal, and the amplifier a2 amplifies and transmits a signal $A_{34}$ made by synthesizing signals produced by the detector cells c3 and c4, and transmits the resultant signal. In mode B, the amplifier a1 amplifies a signal $B_{23}$ made by synthesizing signals produced by the detector cells c2 and c3, and transmits the resultant signal, and the amplifier a2 amplifies a signal $B_{45}$ made by synthesizing signals produced by the detector cells c4 and c5, and transmits the resultant signal.

An amplification factor $A_3$ or $B_3$ for the signal produced by, for example, the detector cell c3 is approximately calculated according to the following expression:

$$A_3(B_3) = (A_{32} + B_{23})/2 - (A_{12} + B_{45})/4$$

Assuming that amplification factors for signals detected by the detector cells c1 to c5 in mode A or B are amplification factors $A_1$ to $A_5$ or $B_1$ to $B_5$, the above expression is grounded on the following:

$$A_3(B_3) = (A_{32} + B_{23})/2 - (A_{12} + B_{45})/4$$
$$= (A_3 + A_4 + B_2 + B_3)/2 - (A_1 + A_2 + B_4 + B_5)/4$$
$$= (A_3 + B_3)/2 + (-A_1 - A_2 + 2B_2 + 2A_4 - B_4 - B_5)/4$$

Herein, since the time instants at which the amplifiers act in mode A are substantially the same as those in mode B, assuming that $A_2$ approximately equals $B_2$, $A_3$ approximately equals $B_3$, $A_4$ approximately equals $B_4$, and $A_5$ approximately equals $B_5$, the right side of the above expression is rewritten as $A_3 + (-A_1 + A_2 + A_4 - A_5)/4$.

Assuming that $\alpha = -A_1 + A_2$ and $\beta = A_4 - A_5$ are established, the right side of the above expression is further rewritten as $A_3 + (\alpha + \beta)/4$. Since the detector cells c1 and c2 are mutually adjoining and the detector cells c4 and c5 are mutually adjoining, $\alpha$ and $\beta$ can be thought to approximately equal 0. Consequently, the right side of the above expression becomes $A_3(B_3)$.

The above calculation is performed by the data processing unit 30b included in the operator console 3 (see FIG. 1). Alternatively, the calculation may be performed by a computer included in the scanner gantry 2, and the result of the calculation may be transferred to the central processing device 30 included in the operator console 3.

Figure 6A:
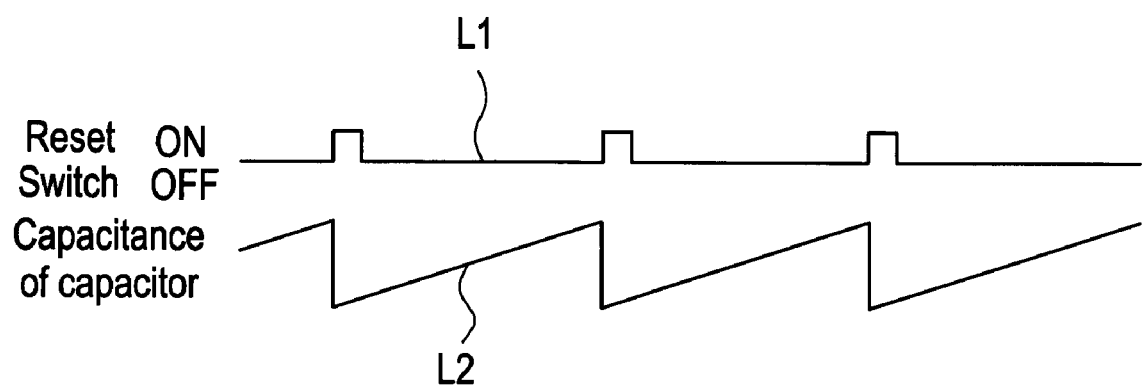
FIGS. 6a and 6b include conceptual diagrams showing a timing of switching modes employed in the X-ray CT system shown in FIG. 1.
Figure 6B:
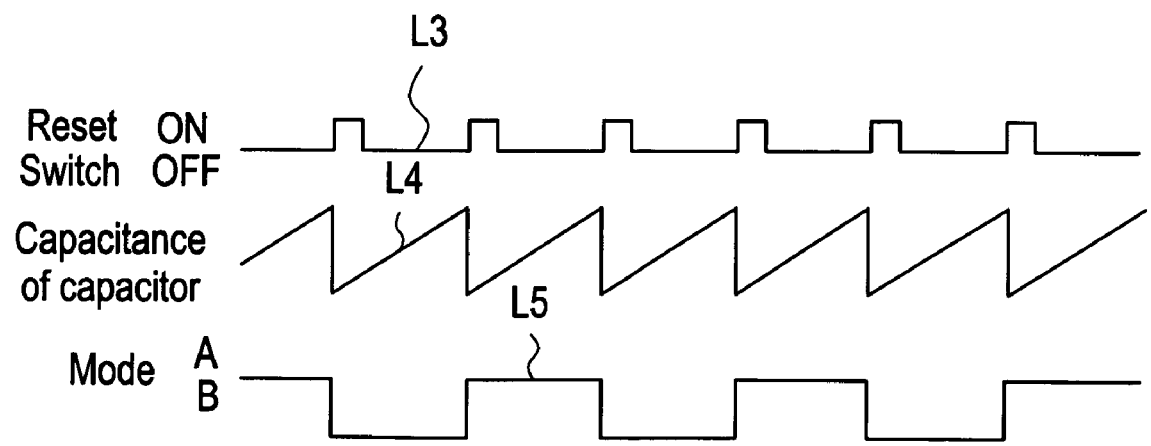

FIG. 6 shows a timing of switching modes A and B. FIG. 6(a) shows a timing of resetting the amplifiers included in a conventional X-ray CT system, and FIG. 6(b) shows a timing of resetting the amplifiers included in the X-ray CT system 1 in accordance with the present embodiment, and the timing of switching the modes. In FIG. 6, the axis of abscissas indicates time.

Referring to FIG. 6(a), as indicated with a solid line L1, a reset switch (corresponding to the switch 60 included in the X-ray CT system 1 shown in FIG. 4) included in the conventional X-ray CT system is turned on at a certain frequency. Consequently, as indicated with a solid line L2, while the reset switch is off, charge is stored in a capacitor (equivalent to the capacitor 59 included in the X-ray CT system 1 shown in FIG. 4) along with transmission of an electric signal from the detector cell 51. When the reset switch is turned on, the charge is released and the amplifier is reset. Thus, an X-ray dose based on which each view is produced is detected.

A frequency at which the reset switch is turned on (a frequency at which a view is produced) is set to a value permitting required precision in images according to conditions including the number of pixels contained in a screen. In general, the reset switch is turned on one thousand times while the X-ray tube and detector rotates by one turn about a subject's body axis.

As shown in FIG. 6(b), in the X-ray CT system 1 in accordance with the present embodiment, the switch 60 is turned at a frequency that corresponds to a double of the frequency adopted in the conventional X-ray CT system. The modes are switched at the same frequency as the frequency at which the switch 60 is turned on, and at the same time of turning on the switch 60.

According to the foregoing embodiment, signals produced by two detector cells 51 are synthesized and amplified by one amplifier 56. Two modes in which different continuities are established between the detector cells 51 and amplifiers 56 are switched. Therefore, the number of amplifiers 56 is decreased to be a half of the number of detector cells 51. Moreover, a dose of X-rays incident on each detector cell 51 can be identified, and precision in detecting X-rays will not be degraded.

Doses are detected at a frequency that corresponds to a double of a frequency at which each view is produced in the conventional X-ray CT system. Even when a distribution of doses is calculated according to an approximate expression that makes distributions of doses recognized in modes A and B identical to each other, that is, even when a distribution of doses is calculated using doses detected over a time over which two views are produced in modes A and B, the same image quality as the image quality ensured conventionally can be maintained.

Since the modes are switched concurrently with resetting of integrating circuits, invasion of noises derived from the mode switching is suppressed.

The present invention is not limited to the aforesaid embodiment but may be implemented in various forms.

As long as the continuities between a plurality of detector elements and a plurality of amplifiers are changed during scanning, the present invention is not limited to the form that detector elements whose signals are combined are changed into others that are partly identical to the detector elements.

Figure 7A:
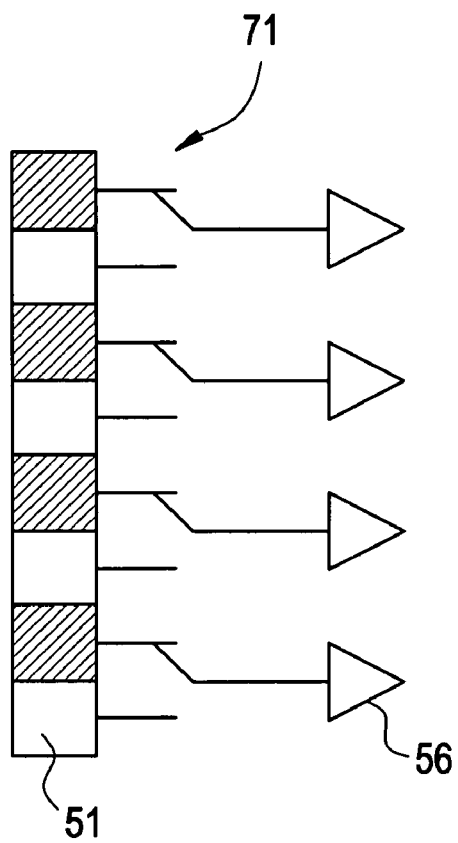
FIGS. 7a and 7b include conceptual diagrams showing a variant of a mode switching method employed in the X-ray CT system.
Figure 7B:
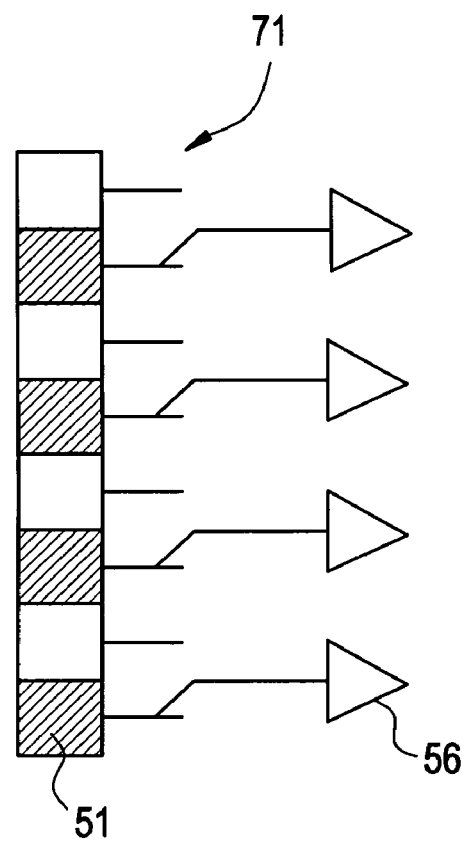

FIG. 7 shows a variant of a mode switching method. In the variant, the continuities between the detector cells 51 and amplifiers 56 are changed so that a mode shown in FIG. 7(a) and a mode shown in FIG. 7(b) will be alternated. Namely, a switching unit 71 selectively connects either of two detector cells 51 to one amplifier 56. Consequently, one amplifier 56 identifies a dose of X-rays incident on each of the two detector cells 51.

When detector elements whose signals are combined are changed into others that are partly identical to the detector elements, amplifications of signals produced by a plurality of detector elements may be assigned to a smaller number of amplifiers than the number of detector elements. The present invention is not limited to the form that a synthetic signal composed of signals produced by two detector elements is amplified by one amplifier.

Figures 8A, 8B, 8C, 8D:
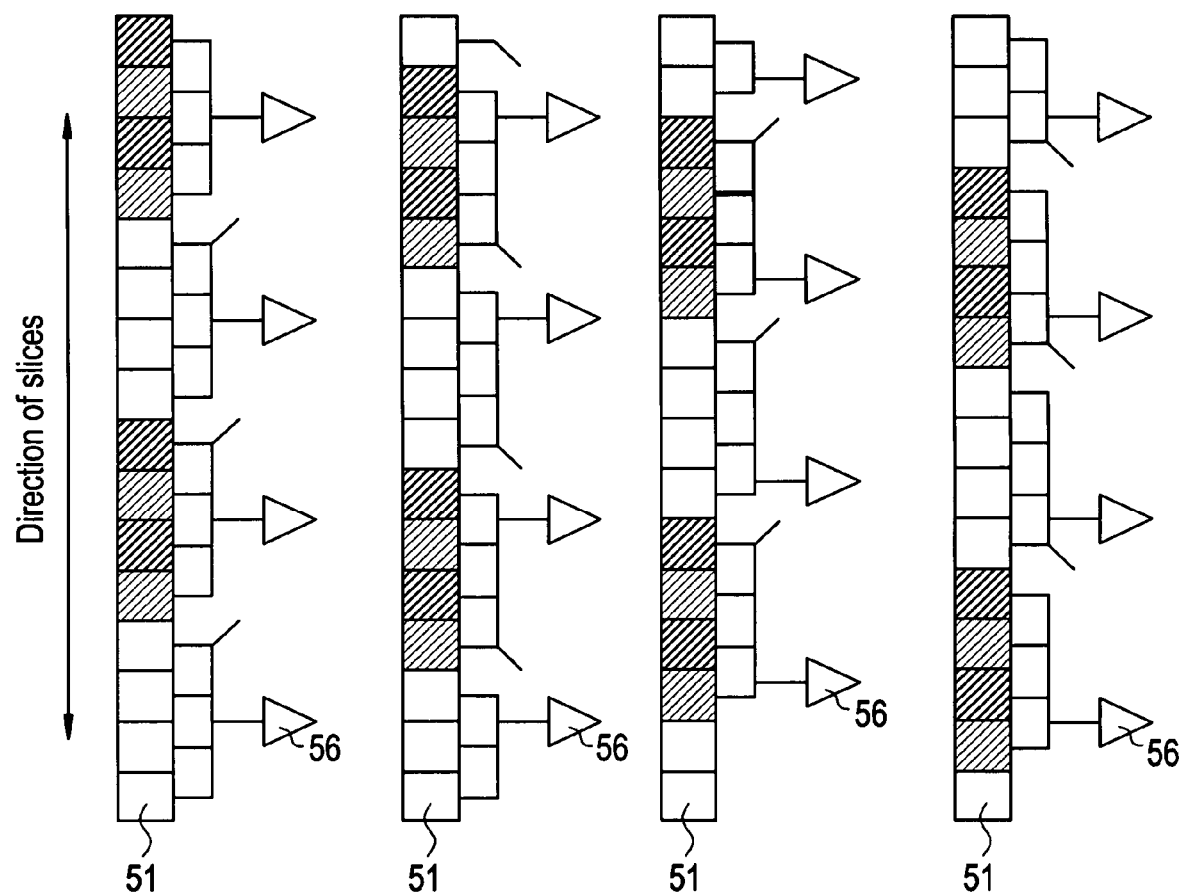
FIGS. 8a and 8b include conceptual diagrams showing another variant of the mode switching method employed in the X-ray CT system.

FIG. 8 shows another variant of a mode switching method. As shown in FIG. 8(*a*) to FIG. 8(*d*), three or more detector cells 51 (four detector cells in FIG. 8) may be grouped together and connected to one amplifier 56, and changed into others juxtaposed in the direction of slices along with the switching of modes. The larger the number of detector elements whose signals are combined is, the smaller the number of amplifiers 56 is. By the way, when the number of detector elements whose signals are combined is small as it is in the aforesaid embodiment, an algorithm for calculating a dose of X-rays incident on each detector element becomes simpler.

Furthermore, when detector elements whose signals are combined are changed into others that are part identical to the detector elements, doses of X-rays incident on a smaller number of detector elements than the number of detector elements whose signals are combined should be identified. The present invention is not limited to the form that detector elements to be grouped together are changed to others that are different from the detector elements in one detector element.

Figure 9A:
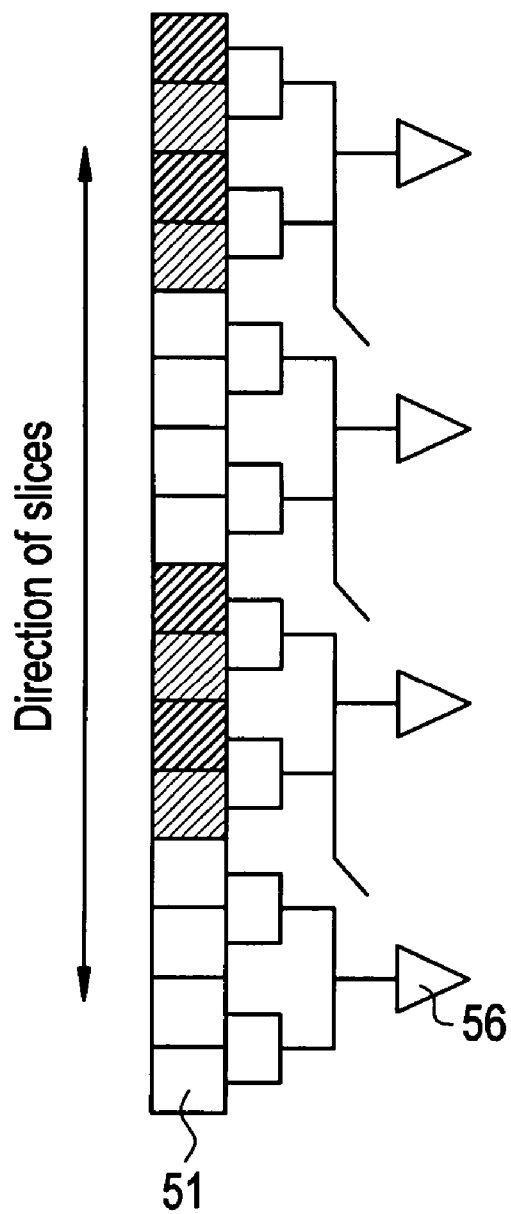
FIGS. 9a and 9b include conceptual diagrams showing another variant of the mode switching method employed in the X-ray CT system.
Figure 9B:
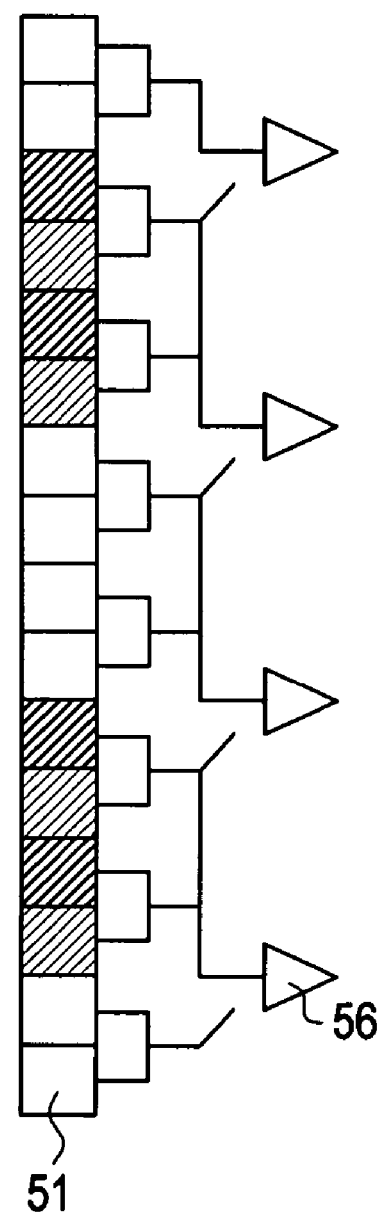

FIG. 9 shows another variant of a mode switching method. As shown in FIG. 9(*a*) and FIG. 9(*b*), two or more detector cells 51 whose signals are combined (two detector cells in FIG. 9) may be changed to others.

An algorithm for calculating doses of X-rays incident on a smaller number of detector elements than the number of detector elements whose signals are combined may be determined appropriately. An approximate expression employed in the present embodiment is a mere example. The approximate expression employed in the embodiment is used to calculate doses on the basis of values detected to produce two views in modes A and B. A distribution of doses to be identified is the same between modes A and B. Values detected to produce views preceding and succeeding the two views may be used for calculation so that different distributions of doses will be identified in modes A and B respectively.

Concrete components of each amplifier or each switching unit may be determined appropriately. For example, the switching unit may include transistors.

When it says that the data acquisition system acquires data items representing doses or the data processing unit identifies a distribution of doses, the values of the doses may not be acquired or identified. Alternatively, pieces of information on doses may be acquired or identified. For example, intensities of signals produced by detector elements may be adopted as pieces of information on doses.

Many widely different embodiments of the invention may be constructed without departing from the spirit and the scope of the present invention. It should be understood that the present invention is not limited to the specific embodiments described in the specification, except as defined in the appended claims.

The invention claimed is:

1. A radiation CT system that scans a subject by rotating about the subject's body axis a radiation source which irradiates radiation to the subject, and that constructs tomographic images of the subject on the basis of a distribution of doses of radiation which are used to produce a plurality of views, the radiation CT system comprising:
    a multi-array detector that has a plurality of detector elements, each of which converts radiation into an electric signal and transmits the electric signal, set in array in a direction of channels that is a direction around the body axis and in a direction of slices that is a direction parallel to the body axis, and that is opposed to the radiation source with the subject between them;
    a data acquisition system that acquires data items representing doses of radiation incident on the multi-array detector on the basis of output signals of the plurality of detector elements; and
    a data processing unit that identifies a distribution of doses of radiation incident on the multi-array detector, which is used to construct the tomographic images, according to the data items acquired by the data acquisition system,
    wherein the data acquisition system includes:
    a plurality of amplifiers that amplifies signals produced by the plurality of detector elements and outputs the amplified signals, wherein a number of the plurality of amplifiers is smaller than a number of the plurality of detector elements; and
    a switching means that changes the continuities between the plurality of detector elements and the plurality of amplifiers so that detector elements whose signals are amplified by each of the plurality of amplifiers will be changed into others juxtaposed in the direction of slices.

2. The radiation CT system according to claim 1, wherein the switching means changes the continuities between the plurality of detector elements and the plurality of amplifiers for each production of a view.

3. The radiation CT system according to claim 2, wherein the switching means changes the continuities between the plurality of detector elements and the plurality of amplifiers so as to cyclically alternate a plurality of modes in which different continuities are established.

4. The radiation CT system according to claim 3, wherein:
    the switching means assigns the plurality of amplifiers to amplifications of signals produced by the plurality of detector elements so that each of the plurality of amplifiers will amplify a signal made by synthesizing signals produced by a predetermined number of detector elements successively juxtaposed in the direction of slices, and changes the continuities between the plurality of detector elements and the plurality of amplifiers so that every time the modes are switched, the predetermined number of detector elements to be assigned to each of the amplifiers will be changed into a predetermined number of detector elements which is partly identical to the predetermined number of detector elements and which is juxtaposed in the direction of slices; and
    the data processing unit calculates a dose of radiation incident on a smaller number of detector elements than the predetermined number of detector elements according to the data items representing doses of radiation incident on predetermined numbers of detector elements that are acquired by the data acquisition system.

5. The radiation CT system according to claim 4, wherein:
    the switching means changes the continuities between the plurality of detector elements and the plurality of amplifiers so that the predetermined number of detector elements to be assigned to each of the amplifiers will be changed into a predetermined number of detector elements that is different from the predetermined number of detector elements in one detector element and that is juxtaposed in the direction of slices; and the data processing unit calculates a dose of radiation incident on each of the detector elements according to the data items representing doses of radiation incident on predetermined numbers of detector elements which are acquired by the data acquisition system.

6. The radiation CT system according to claim 5, wherein the data processing unit accumulates doses of radiation incident on predetermined numbers of detector elements that include a specific detector element and that are grouped in the plurality of modes that is cyclically alternated, subtracts a correction value, which is calculated based on doses of radiation incident on predetermined numbers of detector elements that do not include the specific detector element but that are partly identical to the predetermined numbers of detector elements including the specific detector element, from the result of the accumulation, and calculates a dose of radiation incident on the specific detector element.

7. The radiation CT system according to claim 6, wherein:
the predetermined number of detector elements refers to two detector elements, and the number of modes is two;
the switching means changes the continuities between the plurality of detector elements and the plurality of amplifiers so that a synthetic signal composed of a signal produced by a first detector element and a signal produced by a second detector element, and a synthetic signal composed of a signal produced by a third detector element and a signal produced by a fourth detector element will be amplified in the first mode, and that a synthetic signal composed of a signal produced by the second detector element and a signal produced by the third detector element, and a synthetic signal composed of a signal produced by the fourth detector element and a signal produced by a fifth detector element will be amplified in the second mode; and
assuming that $A_{12}$ denotes a dose of radiation incident on the first and second detector elements in the first mode, $A_{34}$ denotes a dose of radiation incident on the third and fourth detector elements in the first mode, $B_{23}$ denotes a dose of radiation incident on the second and third detector elements in the second mode, and $B_{45}$ denotes a dose of radiation incident on the fourth and fifth detector elements in the second mode, the data processing unit calculates a dose $A_3$ of radiation incident on the third detector element in the first mode according to the following expression:

$$A_3=(A_{34}+B_{23})/2-(A_{12}+B_{45})/4.$$

8. The radiation CT system according to any of claim 7, wherein the switching means changes the continuities between the plurality of detector elements and the plurality of amplifiers so that a synthetic signal composed of a signal produced by a detector element located at an end of a channel extending in the direction of slices and a signal produced by a detector element located at an end of an adjoining channel is amplified in one mode, and that a synthetic signal composed of a signal produced by the detector element located at the end of the channel and a signal produced by a detector element belonging to the channel is amplified in the other mode.

9. The radiation CT system according to any of claim 8, wherein the data acquisition system acquires data at a frequency equivalent to the product of a frequency, at which an ordinary X-ray CT system that does not change the continuities between the plurality of amplifiers and the plurality of detector elements during scanning should produce a view so as to ensure predetermined image quality, by the number of modes, and thus ensures the image quality identical to the predetermined image quality.

10. The radiation CT system according to any of claim 3, wherein the data acquisition system acquires data at a frequency equivalent to the product of a frequency, at which an ordinary X-ray CT system that does not change the continuities between the plurality of amplifiers and the plurality of detector elements during scanning should produce a view so as to ensure predetermined image quality, by the number of modes, and thus ensures the image quality identical to the predetermined image quality.

11. The radiation CT system according to any of claim 4, wherein the switching means changes the continuities between the plurality of detector elements and the plurality of amplifiers so that a synthetic signal composed of a signal produced by a detector element located at an end of a channel extending in the direction of slices and a signal produced by a detector element located at an end of an adjoining channel is amplified in one mode, and that a synthetic signal composed of a signal produced by the detector element located at the end of the channel and a signal produced by a detector element belonging to the channel is amplified in the other mode.

12. The radiation CT system according to any of claim 1, wherein the amplifiers each include an integrating circuit that integrates a signal produced by a detector element, and the switching means performs mode switching concurrently with resetting of the integrating circuits.

13. The radiation CT system according to any of claim 9, wherein the amplifiers each include an integrating circuit that integrates a signal produced by a detector element, and the switching means performs mode switching concurrently with resetting of the integrating circuits.

14. The radiation CT system according to any of claim 13, wherein the switching means includes field-effect transistors.

15. The radiation CT system according to any of claim 14, wherein:
the switching means includes a plurality of switching circuits interposed between the plurality of detector elements and the plurality of amplifiers; and
the switching circuits each include:
a first n-channel field-effect transistor having a source thereof connected to a detector element and having a drain thereof connected to an amplifier;
a second p-channel field-effect transistor having a source thereof connected to the detector element, having a drain thereof connected to the amplifier, and having a gate thereof connected to the gate of the first field-effect transistor; and
an inverter that inverts a signal to be applied to either of the gates of the first and second field-effect transistors.

16. The radiation CT system according to any of claim 1, wherein the switching means includes field-effect transistors.

17. The radiation CT system according to any of claim 1, wherein:
the switching means includes a plurality of switching circuits interposed between the plurality of detector elements and the plurality of amplifiers; and
the switching circuits each include:
a first n-channel field-effect transistor having a source thereof connected to a detector element and having a drain thereof connected to an amplifier;
a second p-channel field-effect transistor having a source thereof connected to the detector element, having a drain thereof connected to the amplifier, and having a gate thereof connected to the gate of the first field-effect transistor; and an inverter that inverts a signal to be applied to either of the gates of the first and second field-effect transistors.

18. A radiation CT system that scans a subject by rotating about the subject's body axis a radiation source which irradiates radiation to the subject, and that constructs tomographic images of the subject on the basis of a distribution of doses of radiation, the radiation CT system comprising:

a multi-array detector tat has a plurality of detector elements, each of which converts radiation into an electric signal and transmits the electric signal, set in array in a direction of channels that is a direction around the body axis and in a direction of slices that is a direction parallel to the body axis, and that is opposed to the radiation source with the subject between them;

a data acquisition system that acquires data items representing doses of radiation incident on the multi-array detector on the basis of output signals of the plurality of detector elements; and a data processing unit that identifies a distribution of doses of radiation incident on the multi-array detector, which is used to construct the tomographic images, according to the data items acquired by the data acquisition system, wherein the data acquisition system includes:

a plurality of amplifiers that amplifies signals produced by the plurality of detector elements and outputs the amplified signals, wherein a number of the plurality of amplifiers is smaller than a number of the plurality of detector elements; and a switching means that assigns the plurality of amplifiers to amplifications of signals produced by the plurality of detector elements so that each of the plurality of amplifiers will amplify a signal made by synthesizing signals produced by a predetermined number of detector elements successively juxtaposed in the direction of slices, and that changes the continuities between the plurality of detector elements and the plurality of amplifiers so that the predetermined number of detector elements assigned to each of the amplifiers will be changed to a predetermined number of detector elements which is partly identical to the predetermined number of detector elements and which is juxtaposed in the direction of slices.

19. A data acquisition system that is included in a radiation CT system in which: a radiation source that irradiates radiation to a subject, and a multi-array detector that has a plurality of detector elements, each of which converts radiation into an electric signal and transmits the electric signal, set in array in a direction of channels that is a direction around the subject's body axis and in a direction of slices that is a direction parallel to the body axis, and that is opposed to the radiation source with the subject between them arc rotated about the subject's body axis in order to scan the subject; and tomographic images of the subject are constructed based on a distribution of doses of radiation which are used to produce a plurality of views, and that acquires data items representing doses of radiation incident on the multi-array detector which are used to construct the tomographic images, comprising:

a plurality of amplifiers that amplifies signals produced by the plurality of detector elements and outputs the amplified signals, wherein a number of the plurality of amplifiers is smaller than a number of the plurality of detector elements; and a switching means that changes the continuities between the plurality of detector elements and the plurality of amplifiers so that detector elements whose signals are amplified by each of the plurality of amplifiers will be changed to others juxtaposed in the direction of slices during scanning of the subject.

20. A data acquisition system that is included in a radiation CT system in which: a radiation source that irradiates radiation to the subject, and a multi-array detector that has a plurality of detector elements, each of which converts radiation into an electric signal and transmits the electric signal, set in array in a direction of channels that is a direction around the subject's body axis and in a direction of slices that is a direction parallel to the body axis, and that is opposed to the radiation source with the subject between them are rotated about the subject's body axis in order to scan the subject; and tomographic images of the subject are constructed based on a distribution of doses of radiation which are used to produce a plurality of views, and that acquires data items representing the doses of radiation incident on the multi-array detector, comprising:

a plurality of amplifiers that amplifies signals produced by the plurality of detector elements and outputs the amplified signals, wherein a number of the plurality of amplifiers is smaller than a number of the plurality of detector elements; and a switching means that assigns the plurality of amplifies to amplifications of signals produced by the plurality of detector elements so that each of the plurality of amplifiers will amplify a signal made by synthesizing signals produced by a predetermined number of detector elements successively juxtaposed in the direction of slices, and that changes the continuities between the plurality of detector elements and the plurality of amplifiers so that the predetermined number of detector elements assigned to each of the amplifiers will be changed to a predetermined number of detector elements which is partly identical to the predetermined number of detector elements and which is juxtaposed in the direction of slices.

* * * * *